United States Patent [19]

Strain

[11] 4,077,265
[45] Mar. 7, 1978

[54] ALCOHOL TESTERS

[76] Inventor: Harvey A. Strain, 715 E. Center, Duncanville, Tex. 75116

[21] Appl. No.: 659,949

[22] Filed: Feb. 20, 1976

[51] Int. Cl.² ............................................. G01N 9/10
[52] U.S. Cl. ........................................................ 73/445
[58] Field of Search ................ 73/442, 444, 445, 452; 137/91; 101/147

[56] References Cited

U.S. PATENT DOCUMENTS

| | | | |
|---|---|---|---|
| 1,937,755 | 12/1933 | Ginger et al. ........................ | 73/444 |
| 2,384,664 | 9/1945 | Westlake .............................. | 73/442 |
| 3,485,257 | 12/1969 | Gegenheimer et al. ............ | 137/91 |
| 3,605,782 | 9/1971 | Hollis et al. ......................... | 73/445 |

*Primary Examiner*—Richard C. Queisser
*Assistant Examiner*—Stephen A. Kreitman

[57] ABSTRACT

The present invention relates to a modification for circulating systems utilized with most alcohol dampening systems on lithographic printing presses and provides a fountain solution testing reservoir which maintains a constant solution level, constantly samples the circulating fountain solution and with the aid of a specific gravity hydrometer and appropriate thermometer gives a continuous, visible, and accurate specific gravity reading of the solution.

3 Claims, 7 Drawing Figures

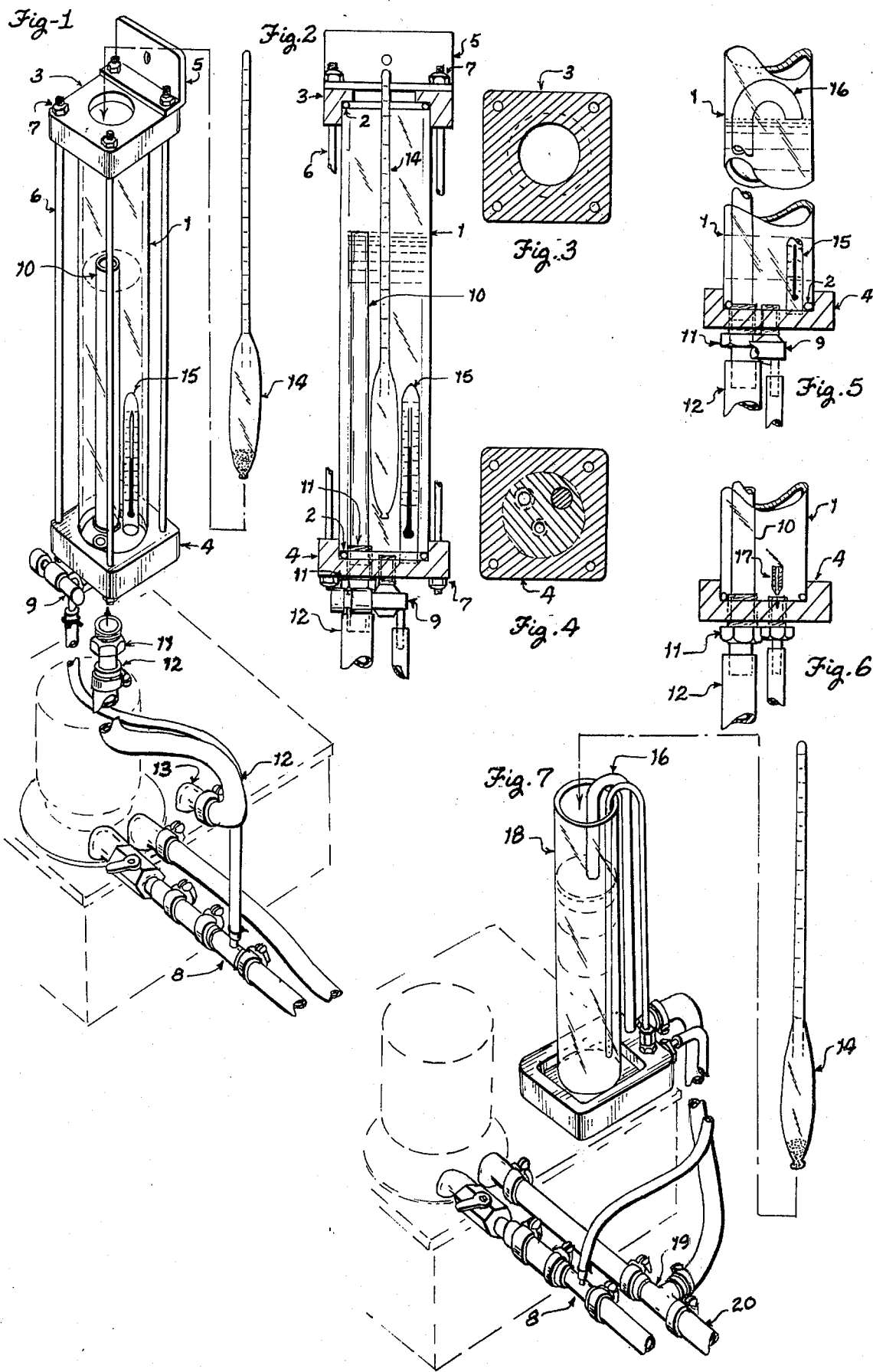

ALCOHOL TESTERS

Conventional alcohol dampening systems (Dahlgren, Harris Microflow, Miehle Matic, Miller Meter, etc.) require that the proper percentages of alcohol, usually 18% to 25% by volume, be mixed initially and added as necessary to compensate for evaporation as the solution circulates and is exposed to the atmosphere. Even though the recommended percentages may be slightly different from one system to another it is important that the percentage does not vary from these recommended percentages due to evaporation, or fluctuations in the printed product will result, causing spoilage.

Most conventional alcohol systems have a circulating reservoir holding from 4 to 10 gallons of mixed solution which varies in depth of solution from 2 inches to 6 inches and circulates water through a water pan which has a depth of only 1 or 2 inches. A circulating pump generates the input flow of solution through a small diameter hose to the water pan of the dampening system and the solution returns through another hose from the water pan back to the reservoir when it reaches a controlled height in the pan providing a constant circulation which is necessary to keep the alcohol mixed properly in the solution. There are no provision or areas in these systems with adequate solution levels to visually test the alcohol percentages with a specific gravity hydrometer requiring: the filling of a glass beaker, usually with yet another container or cup, each time a specific gravity test is made to determine if alcohol percentage is correct; or the use of expensive automatic alcohol testers such as Gray Mills "Alco-Gard", and Baldwin's "Automix", which measure specific gravity and automatically add alcohol. The automatic systems maintain constant specific gravity levels but do not provide a means of visually checking specific gravity and do not compensate for temperature differences which with the same specific gravity reading (for example 0.9719) vary considerably (in this example 10.6%) when the temperature varies from 40° to 86° F. Even though these systems function quite well when operating properly, they do not eliminate the need of periodic hydrometer checks or the need of the present invention to provide the periodic checks as recommended by the suppliers to assure that the automatic system is working properly.

Other systems similar to battery type testers with hydrometers or floating balls inside a syringe are sometimes used but the ineffectiveness of these systems is generally accepted due to inaccurate readings and the breakage factor involved with their use since they cannot be permanently mounted.

The present invention overcomes the existing problems, time, and expense involved in maintaining the proper alcohol percentage by providing a test reservoir where the fountain solution is at a constant and adequate depth to utilize a hydrometer of sufficient length to accurately read specific gravity in the range of 0.900 to 1.000.

The present invention is of additional value in that it constantly samples solution in an area visible to the press operator eliminating the need of manually filling a test beaker every 30 minutes to 2 hours as recommended by suppliers of alcohol dampening systems.

The present invention is of additional value is that it is designed to be permanently mounted in an area convenient to the press operator for ease of operation and to eliminate breakage of the container or hydrometer as experienced quite often in other methods of testing.

The present invention is of additional value since a thermometer is also used to constantly sample temperature in the testing reservoir to give the ultimate in accuracy.

The present invention, due to its simplicity over existing automatic systems, will be more acceptable than automatic systems in many plants that cannot justify the expense of automatic alcohol systems.

The present invention is of additional value due to the fact that even though it is more simple than automatic systems and requires the manual addition of alcohol to the solution, it is more accurate due to the fact that temperature compensations can be easily used to determine accurate alcohol percentages and the fact that the hydrometer serves no additional functions such as pushing levers, closing switches, or operating valves — all of which can affect the accuracy of the hydrometer reading.

The present invention is of additional value in that its use with automatic alcohol control systems will eliminate the need for periodic hydrometer checks as recommended by the suppliers of automatic systems which have no visible test reservoir or transparent control tanks.

These and other objects may be readily discovered upon reading the following specification, in which:

FIG. 1 is a perspective view of the preferred embodiment of the invention.

FIG. 2 is a vertical section view of the preferred embodiment of the invention.

FIG. 3 is a top plan view of the top section of the test reservoir.

FIG. 4 is a top plan view of the base section of the test reservoir.

FIG. 5 is a sectional view of a modified form of the solution heighth/drain function system of the invention.

FIG. 6 is a sectional view of a modified form of the flow control system of the invention.

FIG. 7 is a perspective view of a modified form of the transparent reservoir of the invention.

Referring to the drawings in detail and particularly to FIGS. 1 through 4, the invention consists in the preferred embodiment of a transparent reservoir comprised of the transparent tube 1 sealed by means of "0" rings 2 to the top section 3, the base section 4, and the mounting adaptor 5 by means of threaded rods 6 and nuts 7. A portion of the fountain solution is fed into the reservoir from the pressure output system of the circulating reservoir by means of a bypass connector 8 which is connected to the input/flow control system mechanism 9 of the reservoir which reduces flow turbulence by restriction, providing only sufficient circulation to provide a constant sampling of solution that is typical of the solution in the circulating system. Excessive flow can trap the hydrometer in either a submerged position or cause it to bob, making accurate readings impossible. When the fountain solution reaches the desired heighth as predetermined by the heighth of the drain standpipe 10 inserted in the drain fitting 11 attached to the base section of the reservoir, it is drained by means of an outlet hose 12 connecting the drain fitting to the drain outlet connector 13 attached to the main circulation system reservoir. The top section of the test reservoir provides means to insert a conventional hydrometer 14 to provide a visual specific gravity reading and to insert a thermometer 15 to provide a visible temperature reading enabling the press operator to calculate the exact alcohol percentage with the use of standard charts.

FIG. 5 shows a modified form of the drain/heighth control function mechanism whch vacuums the solution from the reservoir when it reaches a predetermined heighth as determined by the vacuum tube 16, connected to a vacuum function of the circulating system.

FIG. 6 shows a modified form of the input/flow control function utilizing a fixed restrictor 17 in the input system of the reservoir.

FIG. 7 shows a modified form of the transparent reservoir utilizing a transparent container 18 rather than a transparent tube with means of providing the same input/flow function and solution length/drain function as in previous embodiments. FIG. 7 also shows a modified form of drain connection by means of outlet tee 19 which inserts in the drain hose 20 of the central circulating reservoir.

Having thus described the invention, it is to be understood that certain modifications in the construction and arrangement of the parts thereof will be made, as deemed necessary, without departing from the scope of the appended claims.

What I claim is:

1. A device for continuously measuring the specific gravity of an alcohol-water mixture in a lithographic press comprising a test reservoir, means connecting said test reservoir to the main circulating reservoir and water pan of said press, means for controlling and minimizing the turbulence of said input mixture flow into said test reservoir, means within said test reservoir for maintaining a predetermined mixture level, means for measuring the temperature of said mixture within said test reservoir and a free floating hydrometer, means within said test reservoir for measuring the specific gravity of said mixture whereby the temperature measurement is used to correct the specific gravity measurement of said mixture.

2. The device of claim 1 wherein said means for measuring the temperature in said mixture is a thermometer.

3. The device of claim 1 wherein said hydrometer means has a calibrated scale.

* * * * *